United States Patent
Kawai et al.

[11] Patent Number: 5,438,860
[45] Date of Patent: Aug. 8, 1995

[54] CUTTER BIT ABRASIVE DETECTING DEVICE OF SHIELD MACHINE

[75] Inventors: Kazunari Kawai; Hiroshi Miura, all of Hirakata, Japan

[73] Assignee: Kabushiki Kaisha Komatsu Seisakusho, Tokyo, Japan

[21] Appl. No.: 120,725

[22] Filed: Sep. 13, 1993

[30] Foreign Application Priority Data

Dec. 18, 1992 [JP] Japan .............. 4-091594 U

[51] Int. Cl.⁶ ............................................. G01N 3/56
[52] U.S. Cl. .................................. 73/7; 451/6; 408/16
[58] Field of Search .............. 73/7, 104; 408/16; 51/165.2, 165.74; 451/6, 8

[56] References Cited

U.S. PATENT DOCUMENTS

| | | | |
|---|---|---|---|
| 4,091,654 | 5/1978 | Hurtig et al. | 73/7 |
| 4,370,834 | 2/1983 | Habib | 73/600 X |
| 4,420,253 | 12/1983 | Pryor | 408/16 X |
| 4,558,686 | 12/1985 | Ono | 51/165.72 X |
| 4,667,113 | 5/1987 | Nakajima et al. | 408/16 X |
| 4,748,988 | 6/1988 | Green et al. | 73/7 X |
| 4,884,434 | 12/1989 | Satake et al. | 73/7 |

FOREIGN PATENT DOCUMENTS

60-151996 10/1985 Japan .

*Primary Examiner*—Thomas P. Noland
*Attorney, Agent, or Firm*—Flynn, Thiel, Boutell & Tanis

[57] ABSTRACT

In a cutter bit abrasion detecting device of a shield excavator comprising a plurality of cutter bits arranged on the front surface of a cutter head rotatably provided in front of a shield body for excavating a working place, a sensor hole or sensor holes are formed in each of some of the cutter bits and sensor heads each comprising a U-shaped single-core optical fiber accommodated in a casing are inserted thereinto. As a result, sensor heads can be thin to be easily inserted into the sensor holes having a small diameter so as to be set in cutter bits with ease since the single-core optical fiber is employed and the attenuation of light received by the sensor head can be reduced due to the attenuation of light between a reflector plate and the optical fiber since no reflector plate is employed, so that accuracy in detection is improved.

4 Claims, 10 Drawing Sheets

CUTTER BIT ABRASIVE DETECTING DEVICE OF SHIELD MACHINE

BACKGROUND OF THE INVENTION

1. Field of the Invention

The present invention relates to a cutter bit abrasion detecting device of a shield machine for detecting the abrasion of cutter bits provided on a cutter head.

2. Prior Art

A conventional shield machine for excavating a tunnel comprises a cutter head rotatably provided in front of a shield body and a plurality of cutter bits for excavating a working place which are radially arranged and mounted thereon.

When such a shield machine as set forth above excavates gravel or sandy beds, the cutter bits are rapidly worn away.

Accordingly in case of the conventional shield machine, the time for exchanging the cutter head is estimated beforehand based on an empirical formula corresponding to the soil to be excavated and the worn-out cutter bits are replaced with new ones from inside the shield body at the time of exchange during the excavation.

This method, however, has a drawback in that an error occurs between the actual time of exchange and the estimated one if the excavated soil is different from supposed one.

In order to improve such a drawback, an abrasion detecting device for detecting the abrasion of cutter bits using optical fibers is disclosed in the Japanese Utility Model Laid-Open Publication No. 60-51996. The abrasion detecting device set forth above detects the stop of signal caused by the breakage of the optical fibers due to the abrasion of cutter bits, wherein a plurality of optical fibers are folded back in a U shape and the tip end of the U-shaped optical fibers are inserted into a hole formed in one of the cutter bits. The optical fibers need to have a large radius of curvature at the folded back portion thereof in order to prevent them from being broken. As a result, the hole needs to have a large diameter to accommodate the U-shaped optical fibers therein, which lowers the strength of the cutter bit per se so that the cutter bit is liable to be broken in excavation.

Moreover, the conventional abrasion detecting device also has a drawback such that it cannot detect the abrasion of a shank to which the chip is fixed since the number of holes into which the optical fibers can be inserted in one cutter bit is limited due to the large diameter thereof.

Another cutter bit abrasion detecting device equipped with a reflector plate at the tip end of the optical fibers for reflecting light thereby is also proposed in order to improve such drawbacks.

Figure 11:
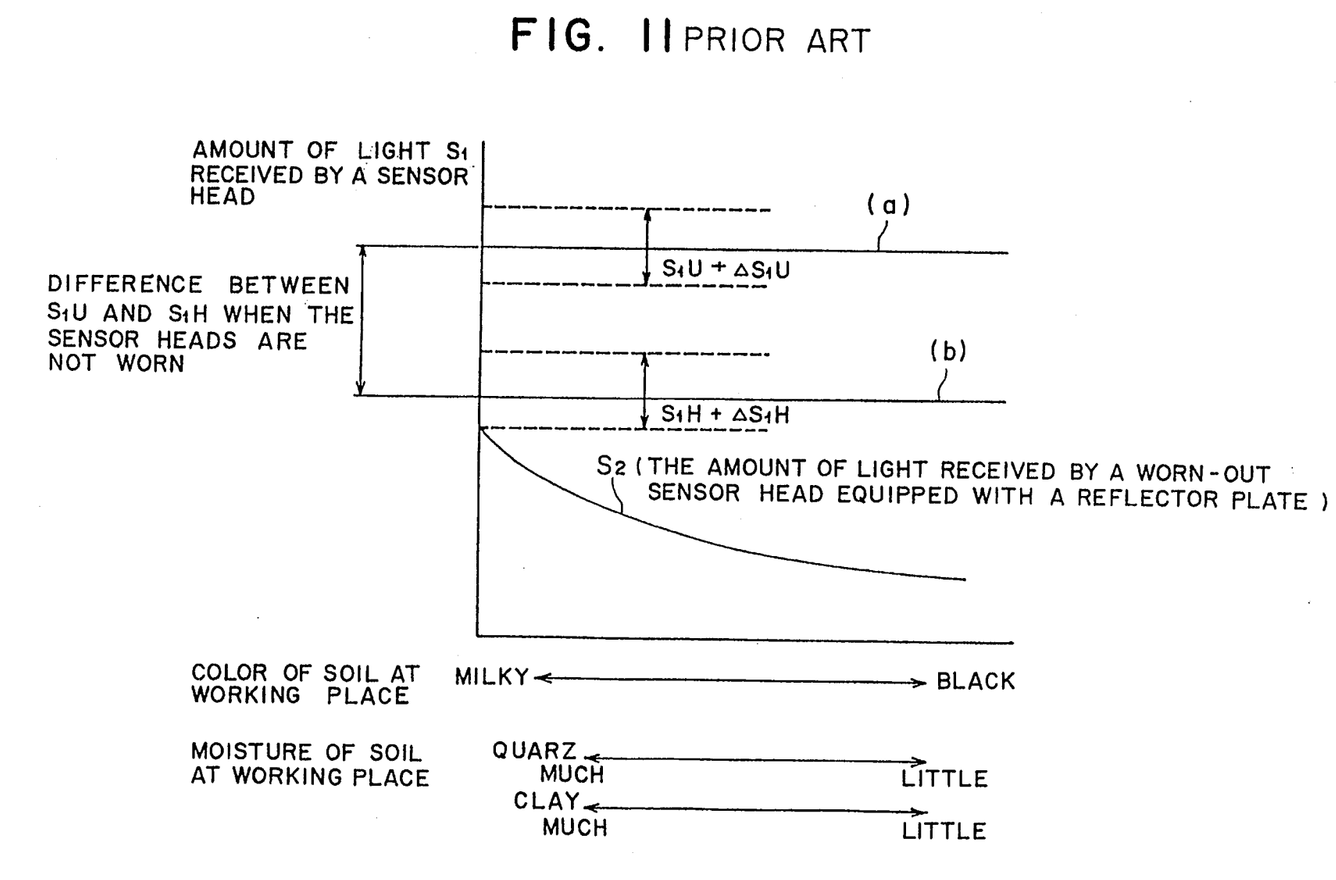
FIG. 11 is a diagram of the amount of light received by sensor heads in a conventional abrasion detecting device.

The sensor head equipped with a reflector plate at the tip end of the optical fiber, however, has a drawback in that the amount of light $S_1$ received thereby is remarkably reduced compared with the sensor head comprising a U-shaped optical fiber due to the attenuation of light as it is propagated in the air as illustrated in FIG. 11.

In FIG. 11, denoted at (a) is the amount of light $S_1U$ received by the sensor head comprising the U-shaped optical fiber, (b) is the amount of light $S_1H$ received by the sensor head equipped with the reflector plate and $S_2$ represents the variation of light received by the sensor head equipped with the reflector plate as the sensor head is worn away.

When the cutter bit is worn away, the amount of light received by the sensor head varies according to the colors or ingredients of soil due to irregular reflection thereof in the working place.

That is, as illustrated in FIG. 11, the amount of light received by the sensor head increases according to the whiteness of soil, decreases according to the darkness of soil, increases when the soil contains much quartz or clay and decreases when the soil contains little quartz or clay.

SUMMARY OF THE INVENTION

The present invention has been made in order to improve the drawbacks of the aforementioned conventional abrasion detecting device and aims to provide a shield machine cutter bit abrasion detecting device which can be plugged in a cutter bit with ease and moreover is capable of detecting the abrasion of chips or shanks with accuracy.

In order to attain the above object, the present invention provides a cutter bit abrasion detecting device of a shield machine comprising a plurality of cutter bits 4 arranged on the front surface of a cutter head 3 rotatably provided in front of a shield body 1 for excavating a working place, wherein a sensor hole or sensor holes 4c are formed in each of some of said cutter bits 4 and sensor heads each comprising a U-shaped single-core optical fiber accommodated in a casing are inserted thereinto.

With the arrangement set forth above, the sensor head according to the present invention is improved in detecting accuracy since the amount of light received thereby is not attenuated as in that sensor head equipped with a reflector plate at the tip end of the optical fibers, and moreover, it can be inserted with ease into a sensor hole having a small diameter.

PREFERRED EMBODIMENT OF THE INVENTION

An embodiment of the present invention will be described hereinafter with reference to the drawings.

Figure 1:
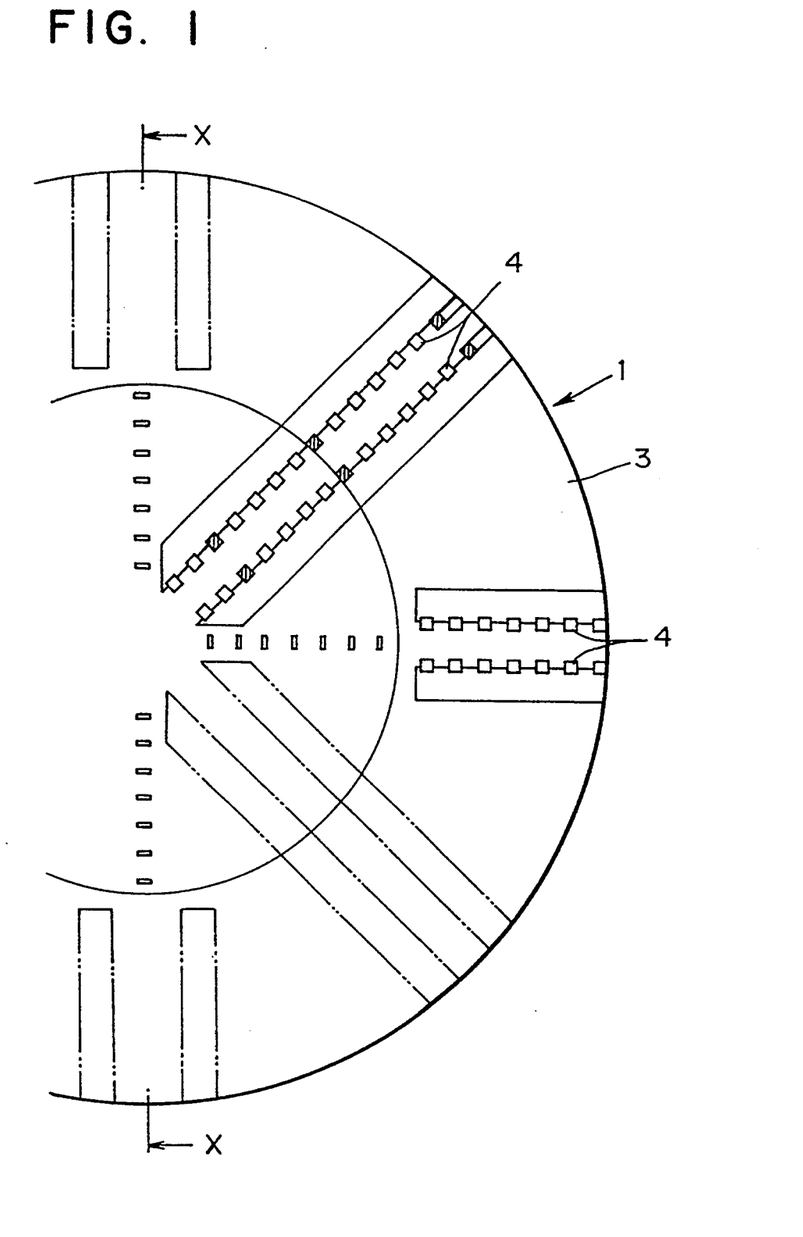
FIG. 1 is a front view of a shield machine according to an embodiment of the present invention.
Figure 2:
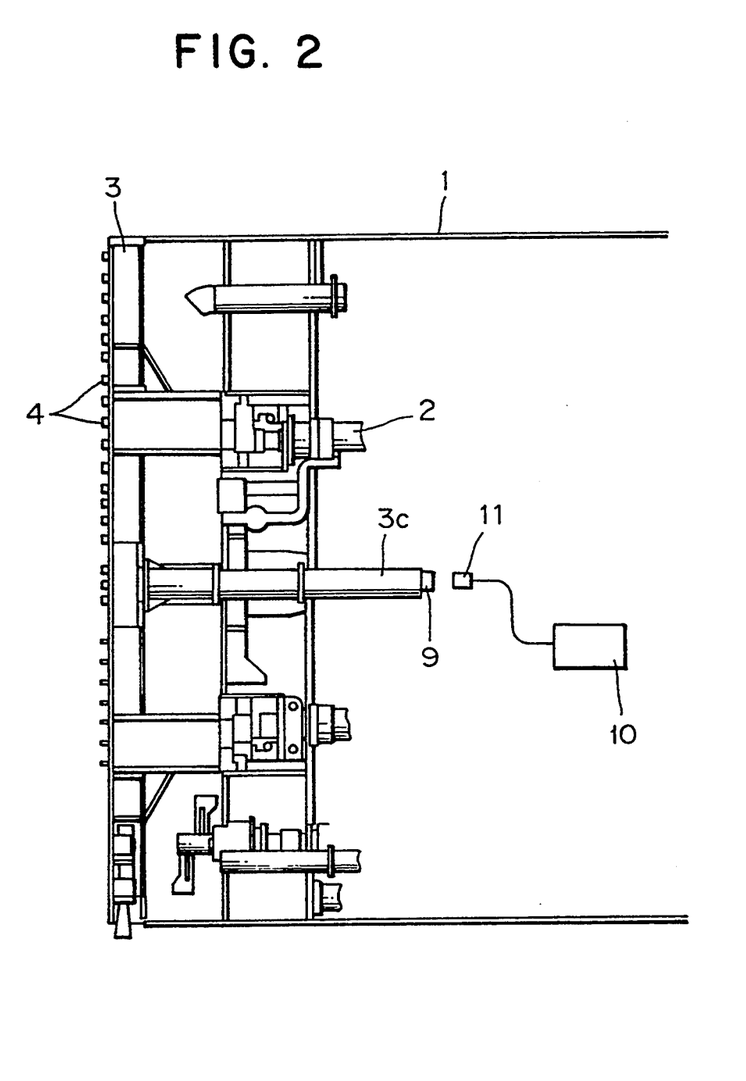
FIG. 2 is a cross-sectional view taken along the line X—X of FIG. 1.

FIGS. 1 and 2 respectively are front and cross-sectional views showing a shield machine according to the embodiment of the present invention, wherein a shield body is denoted at 1.

A cutter head 3 which is rotated by a cutter head motor 2 is provided in front of the aforementioned shield body 1 and a plurality of cutter bits 4 are detachably attached to the front surface of the cutter head 3 for excavating a working place as a consequence of the rotation of the cutter head 3.

Figure 3:
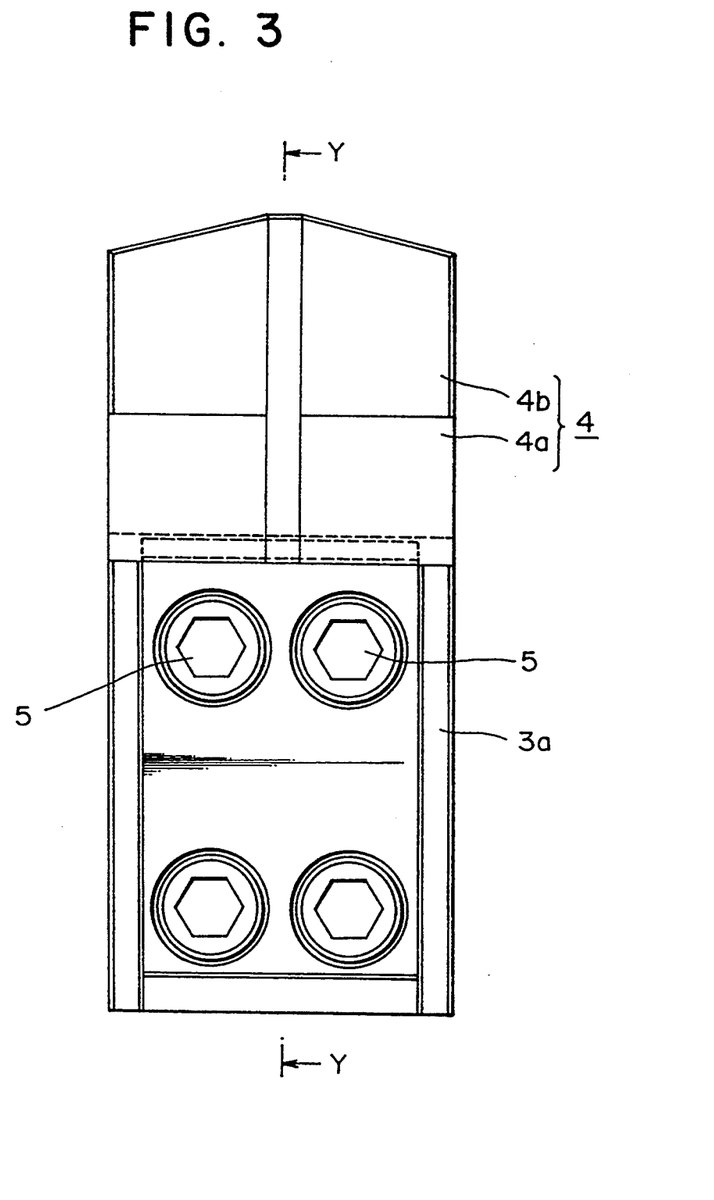
FIG. 3 is a front view of a cutter chip in FIG. 1.
Figure 4:
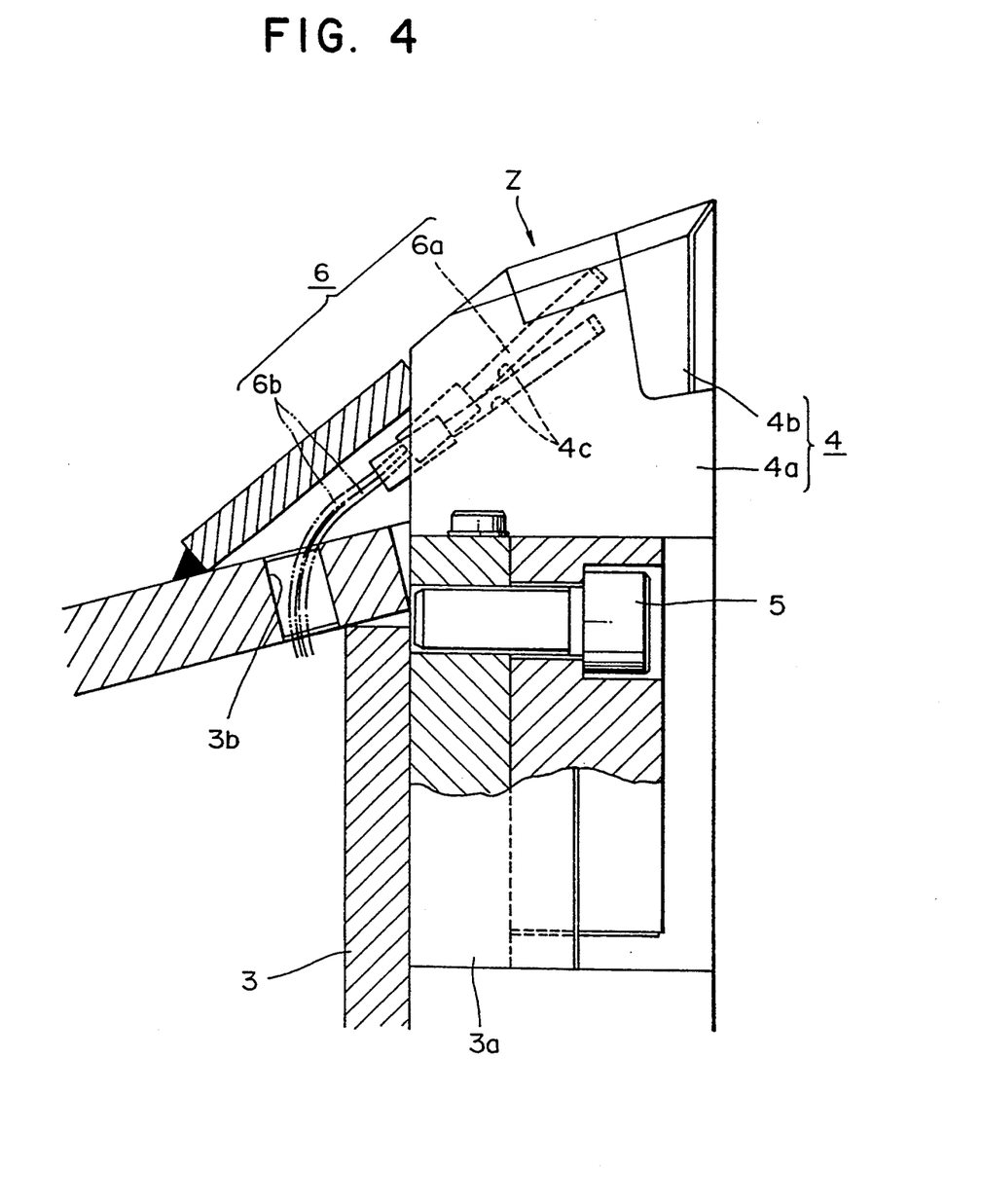
FIG. 4 is a cross-sectional view taken along the line Y—Y of FIG. 3.
Figure 5:
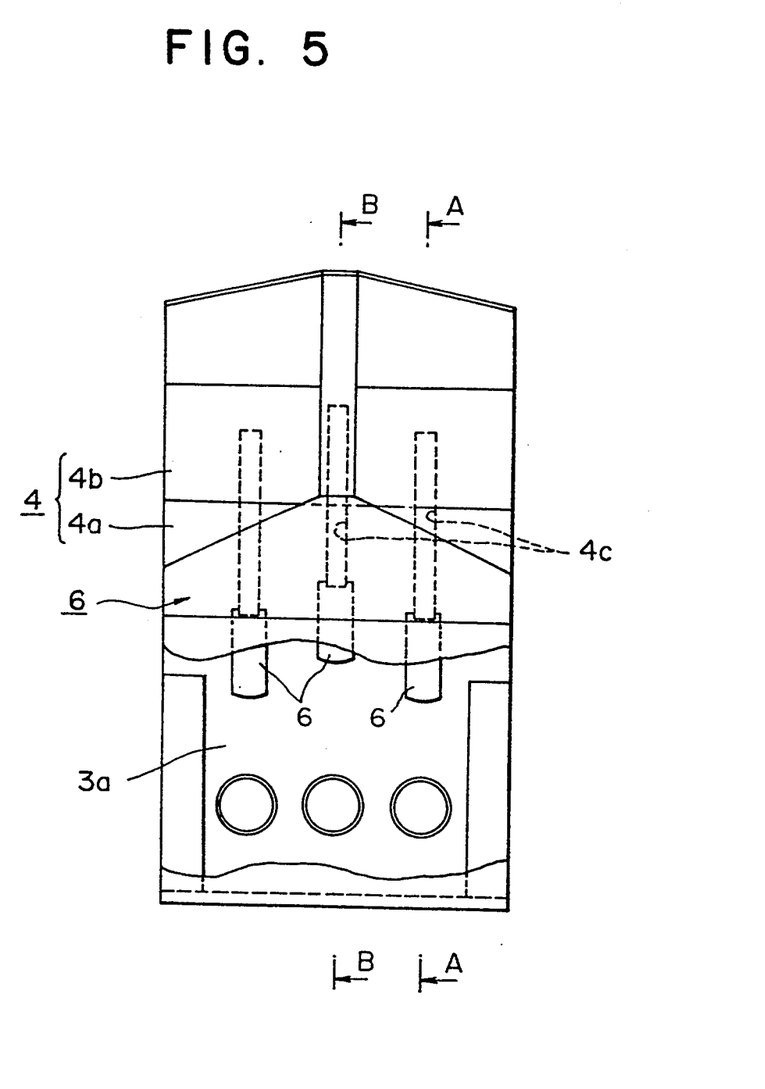
FIG. 5 shows the cutter chip viewed in the direction of Z of FIG. 4.

As illustrated in FIG. 3, the cutter bit 4 set forth above is composed of a shank 4a and a cemented carbide chip 4b fixedly mounted on the tip end of the shank 4a which is inserted into a holder 3a provided on the cutter head 3 at the shank 4a thereof and is fixed to the holder 3a by fixing members 5. Among the cutter bits 4, for example, 3 to 5 of those which are arranged radially serve as abrasion detecting bits, in which a plurality of, e.g. three, sensor holes or bores 4c are bored through the shank 4a and the cemented carbide chip 4b.

Figure 6:
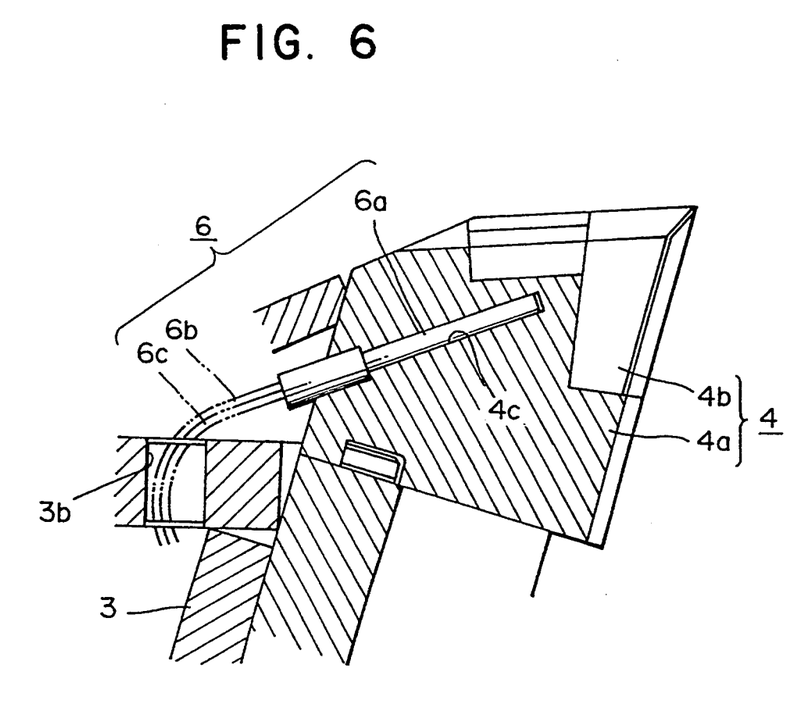
FIG. 6 is a cross-sectional view taken along the line A—A of FIG. 5.
Figure 7:
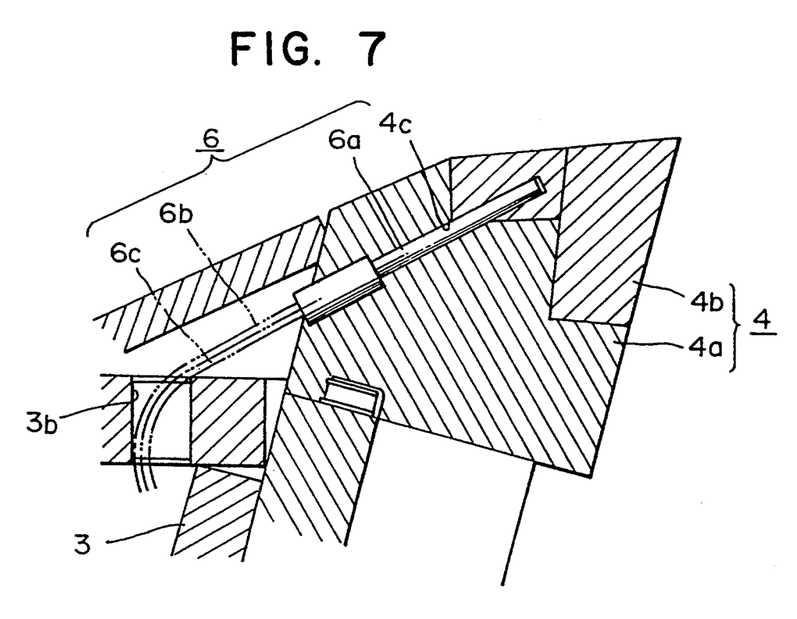
FIG. 7 is a cross-sectional view taken along the line B—B of FIG. 5.

The sensor holes 4c positioned on both sides of the cutter bit 4 do not extend get out of the shank 4a as illustrated in FIG. 6 while the central sensor hole 4c reaches inside the cemented carbide chip 4b passing through the shank 4a as illustrated in FIG. 7.

The sensor heads 6a of abrasion detecting sensors 6 are inserted into these sensor holes 4c.

Figure 9:
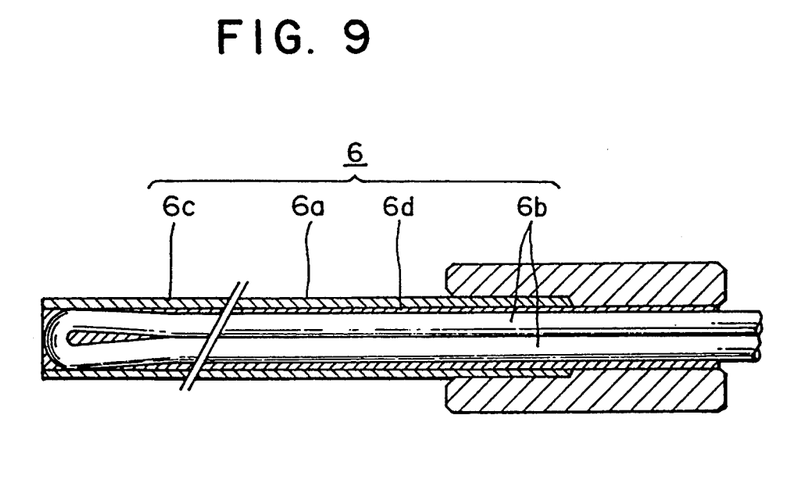
FIG. 9 is a view showing in detail an abrasion detecting sensor employed by the abrasion detecting device in FIG. 8.

The abrasion detecting sensor 6 comprises a single-core optical fiber 6b, i.e. a fiber optic unit 6b, which is folded back to form a shape of a U and a casing 6c into which the U-shaped single-core optical fiber 6b is inserted until the tip end of the U-shaped single-core optical fiber 6b reaches the tip end of the casing 6c and which is filled with resin 6d so as to incorporate the casing 6c and the optical fiber 6b into the sensor head 6a thereof as illustrated in FIG. 9.

The sensor head 6a having the arrangement as set forth above is pushed into the sensor hole 4c through the opening at the base portion of the shank 4a to be fixed to the cutter bit 4 by filling the sensor hole 4c with epoxy resin and the like while the optical fiber 6b extending from the sensor head 6a is introduced into the cutter head 3 through an introducing hole 3b perforated in the cutter head 3.

Figure 8:
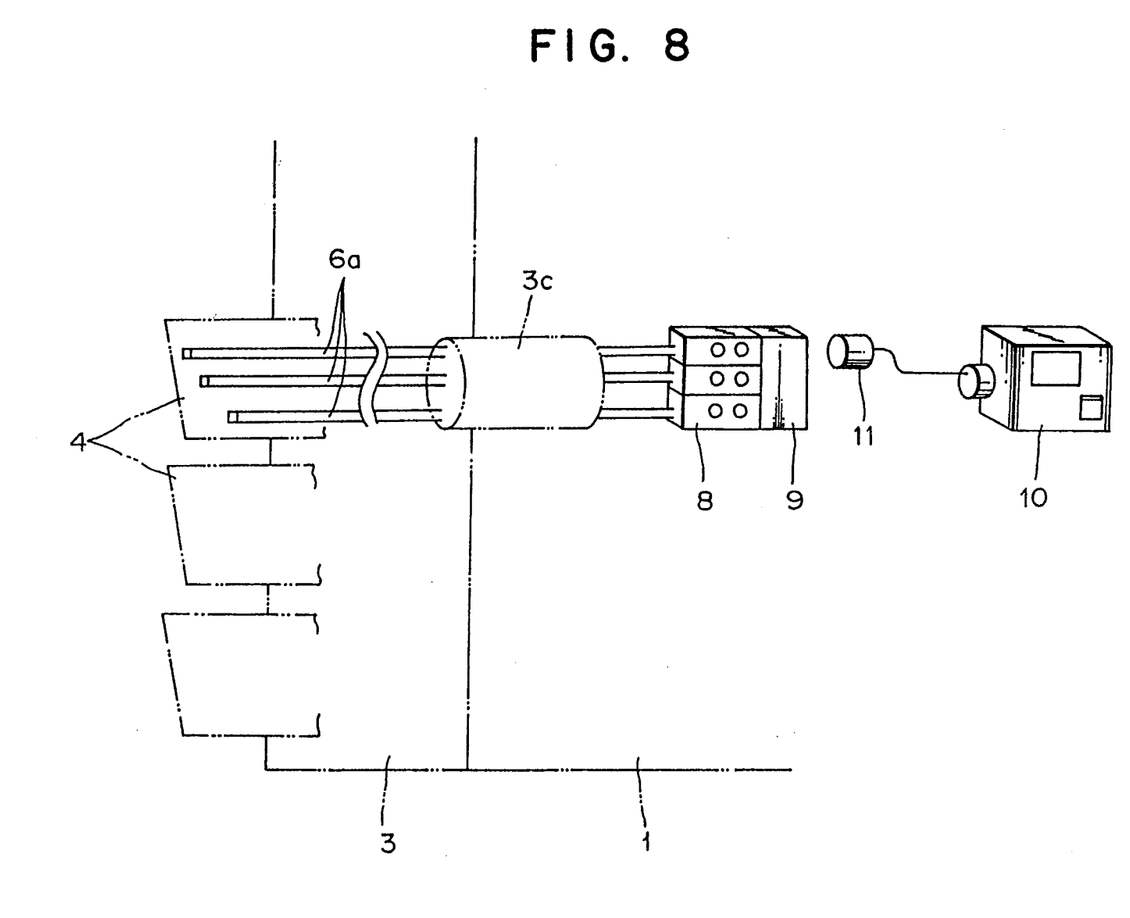
FIG. 8 is a view showing the arrangement of an abrasion detecting device according to the embodiment of the present invention.

The optical fiber 6b introduced into the cutter head 3 passes through a center shaft 3c provided for rotatably supporting the cutter head 3 and is coupled to a converter 9 by way of an amplifier provided at the rear end of the center shaft 3c as illustrated in FIG. 8.

A portable abrasion detecting unit 10 having a power source is coupled to the converter 9 by way of a connector 11.

The operation of the abrasion detecting device will be described hereinafter. A plurality of cutter bits 4 fixed to the front surface of the cutter head 3 excavate the working place as the shield body 1 advances, but the cemented carbide chips 4b and the shank 4a of the cutter bits 4 are worn away after long excavation.

Detecting the abrasion of the cutter bits 4 is performed as follows after coupling the abrasion detecting unit 10 to the converter 9 at the rear end of the center shaft 3c while the cutter head 3 is stopped.

When the cutter bit is not so worn away, the amount of light inputted into the sensor head 6a is almost equal to that emitted therefrom since the incident light at one end of the optical fiber 6b reaches the folded portion of the sensor head 6a and is sent back therefrom intact through the other end of the optical fiber 6b to the abrasion detecting unit 10. When the tip end of the cemented carbide chip 4b is worn away by the amount $\delta 1$ in FIG. 10, the tip end of the sensor head 6a set in the cemented carbide chip 4b is also worn away therewith so that the amount of light emitted from the sensor head 6a in the cemented carbide chip 4b is reduced.

Figure 10:
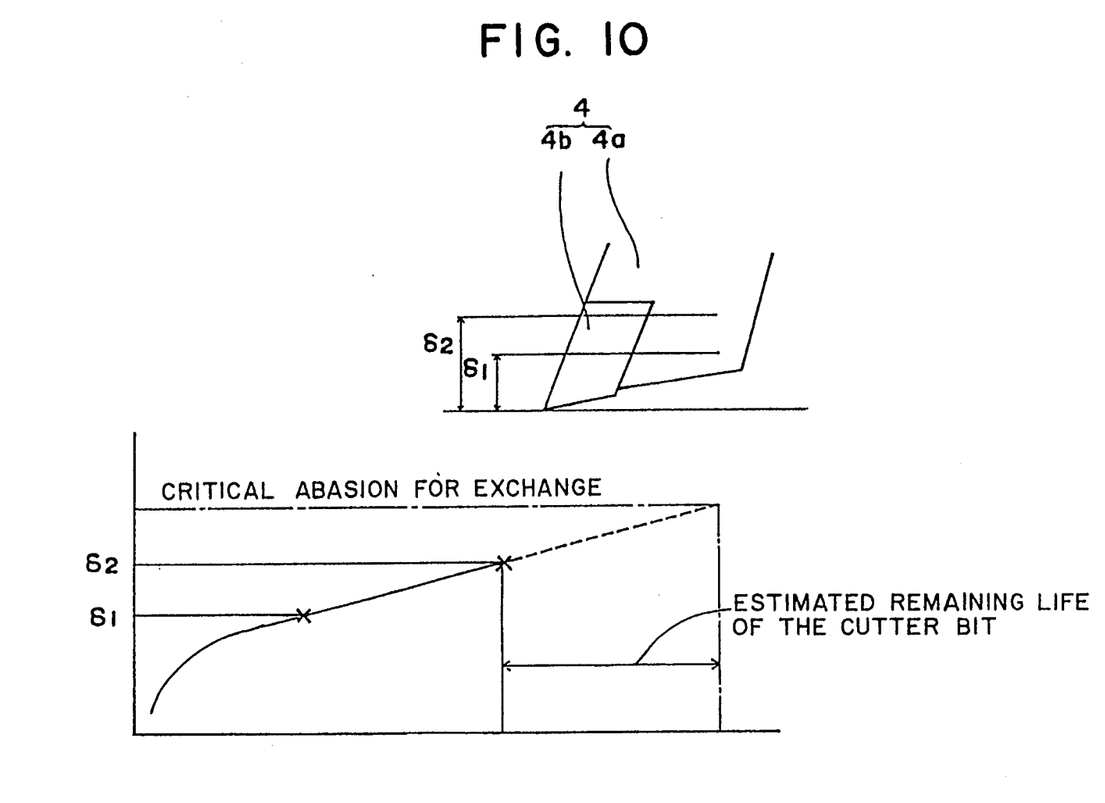
FIG. 10 is a view for explaining the operation of the abrasion detecting device in FIG. 8.

When the abrasion advances further by the amount $\delta 2$ in FIG. 10, the sensor heads 6a set in the shank 4a are also worn away so that the amount of light emitted therefrom is also reduced.

When the abrasion detecting unit 10 detects that the abrasion of the cutter bit 4 reaches the critical abrasion for exchange as illustrated in FIG. 10, the cutter bit 4 is replaced with a new one so that the exchange of the cutter bit 4 is performed on the basis of actual abrasion thereof.

A single-core optical fiber composed of a polyethylene-coated acrylic resin (PMMA resin) which can be small in allowable curvature radius is employed for the single-core optical fiber 6b of the sensor head 6a.

The maximum diameter of the outer periphery of the U-shaped folded portion is set to be less than 2.5 times the diameter of the outer periphery of the single-core optical fiber including the coating thereof and the folded portion is fixed in resin so as to prevent the same from varying in curvature.

In this way it is possible to miniaturize the outer periphery of the sensor head 6a on the order of $\phi 6.4$.

As described above in detail, according to the present invention, inasmuch as each sensor head comprising a U-shaped single-core optical fiber is inserted into each sensor hole formed in the cutter bit and the sensor hole consequently can be smaller than that of a conventional abrasion detecting device into which a plurality of optical fibers are inserted, troubles such as the breakage of the cutter bit during excavation due to reduced strength thereof can be eliminated. Moreover, a plurality of abrasion detecting sensors can be set in one cutter bit so that the abrasion thereof can be detected in steps and the time of exchanging the cutter bit can be properly determined.

Furthermore, since the sensor head does not employ a reflector plate so that it is influenced less by the diffusion or irregular reflection of light due to muddy water or excavated soil than that employing the reflector plate even if the sensor head is worn away, it can have a large signal-to-noise ratio (S/N), which lessens erroneous operations so as to improve the reliability of the device.

What is claimed is:

1. A cutter bit abrasion detecting device of a shield machine comprising:
   a plurality of cutter bits arranged on a front surface of a cutter head rotatably provided in front of a shield body for excavating a working place;
   at least one sensor hole formed in at least one of said cutter bits; and
   at least one sensor head inserted within each said sensor hole formed in said cutter bit, each said sensor head comprising a single fiber optic unit folded in a U-shape and accommodated in a casing, said fiber optic unit being a single-core optical fiber for transmitting light therethrough covered by a polyethylene-coated acrylic resin coating.

2. A cutter bit abrasion detecting device according to claim 1, wherein said single-core fiber optic unit and said polyethylene-coated acrylic resin coating have a reduced allowable curvature radius which may be attained without breaking so as to be employed for each fiber optic Unit of said sensor head.

3. A cutter bit abrasion detecting device for a shield machine which has a shield body and a cutter head rotatably mounted to and disposed proximate a forward end of said shield body for excavating a working place, said cutter bit abrasion detecting device comprising:
 a plurality of sensor heads for detecting wear each comprising a hollow casing which defines a tip end thereof and a single fiber optic unit folded in a U-shape to define a folded end thereof, said fiber optic unit received within said casing with said folded end disposed proximate said tip end, said single fiber optic unit comprising a single-core optical fiber and a polyethylene-coated acrylic resin coating covering said single-core optical fiber; and
 a plurality of cutter bits arranged on a front surface of said cutter head for said excavating, at least one of said cutter bits having a plurality of sensor bores formed therein corresponding to said plurality of sensor heads, each said sensor bore formed in said cutter bit extending from an open end through a predetermined distance in a forward direction and terminating at a sensor end, said sensor ends of at least two of said sensor bores offset one from the other in said forward direction so as to be exposed at different stages of wear of said cutter bit during said excavating, each said sensor bore receiving one of said sensor heads therein with said tip end thereof disposed proximate said sensor end to indicate said stage of wear of said cutter bit as said folded end in said tip end is worn away.

4. A cutter bit abrasion detecting device according to claim 3, wherein each said cutter bit includes a shank and a cutting chip fixed to a forward end of said shank, at least a first of one of said sensor bores extending into said shank and terminating at said sensor end thereof and at least a second one of sensor bores extending forwardly beyond said first sensor bore into said cutting chip and terminating at said sensor end thereof.

* * * * *